United States Patent [19]

Seifert et al.

[11] Patent Number: 5,045,061

[45] Date of Patent: Sep. 3, 1991

[54] BALLOON CATHETER AND LOCKING GUIDEWIRE SYSTEM

[75] Inventors: C. Vaughan Seifert, Boxborough; Wolcott M. Downey, Melrose; Peter J. Shank, Burlington, all of Mass.

[73] Assignee: C. R. Bard, Inc., Murray Hill, N.J.

[21] Appl. No.: 474,371

[22] Filed: Feb. 2, 1990

[51] Int. Cl.[5] .......................................... A61M 29/00
[52] U.S. Cl. ........................................ 604/96; 604/95; 604/283; 128/772; 606/194
[58] Field of Search .................... 604/95, 96, 283; 128/656–658, 772; 606/192, 194, 7

[56] References Cited

U.S. PATENT DOCUMENTS

| | | | |
|---|---|---|---|
| 4,490,421 | 12/1984 | Levy | 604/96 X |
| 4,545,390 | 10/1985 | Leary | 128/772 |
| 4,554,929 | 11/1985 | Samson et al. | 128/772 |
| 4,573,470 | 3/1986 | Samson et al. | 604/96 X |
| 4,616,653 | 10/1986 | Samson et al. | 684/96 X |
| 4,641,654 | 2/1987 | Samson et al. | 128/344 |
| 4,646,742 | 3/1987 | Packard et al. | 606/194 |
| 4,726,374 | 2/1988 | Bales et al. | 606/194 X |
| 4,790,331 | 12/1988 | Okada et al. | 128/772 |
| 4,800,890 | 1/1989 | Cramer | 128/657 |
| 4,815,478 | 3/1989 | Buchbinder et al. | 128/772 |
| 4,827,941 | 5/1989 | Taylor et al. | 128/657 |
| 4,846,174 | 7/1989 | Willard et al. | 606/194 |
| 4,848,344 | 7/1989 | Sos et al. | 606/194 |
| 4,957,117 | 9/1990 | Wysham | 604/95 |

Primary Examiner—C. Fred Rosenbaum
Assistant Examiner—Adam J. Cermak
Attorney, Agent, or Firm—Wolf, Greenfield & Sacks

[57] ABSTRACT

A low profile, steerable balloon dilatation catheter for dilating obstructions in blood vessels is provided which also enables catheter exchanges to be performed without losing guidewire position. The system includes a guidewire and catheter that can be locked together to be operated in a manner as that of an integral wire catheter, or alternatively, they can be unlocked to allow the guidewire to be operated independently in a manner similar to that of an over-the wire catheter system. In the latter mode of operation, the length of the guidewire, at its proximal end, can be extended and the catheter can be withdrawn from the patient without causing a loss of guidewire position. With the guidewire position so maintained, a succeeding catheter can be advanced over the guidewire to the vascular location being treated.

25 Claims, 2 Drawing Sheets

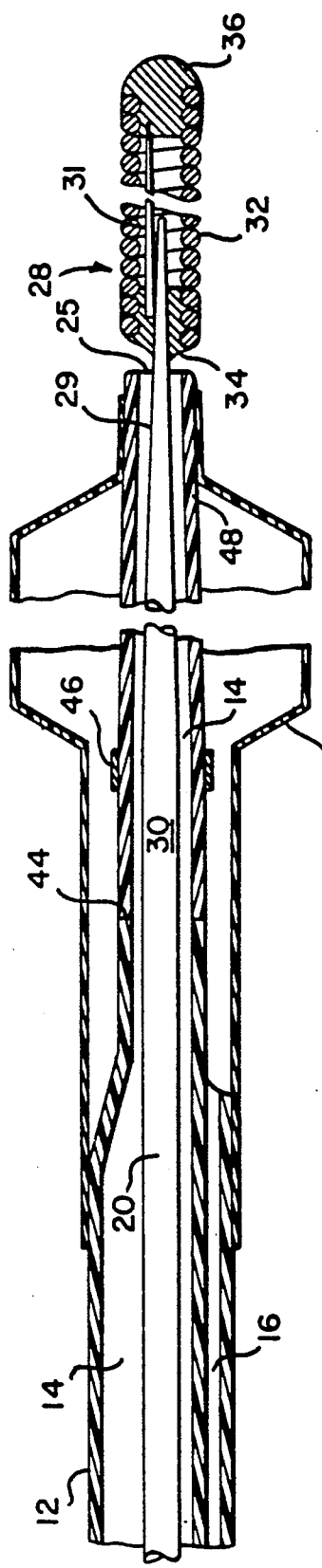
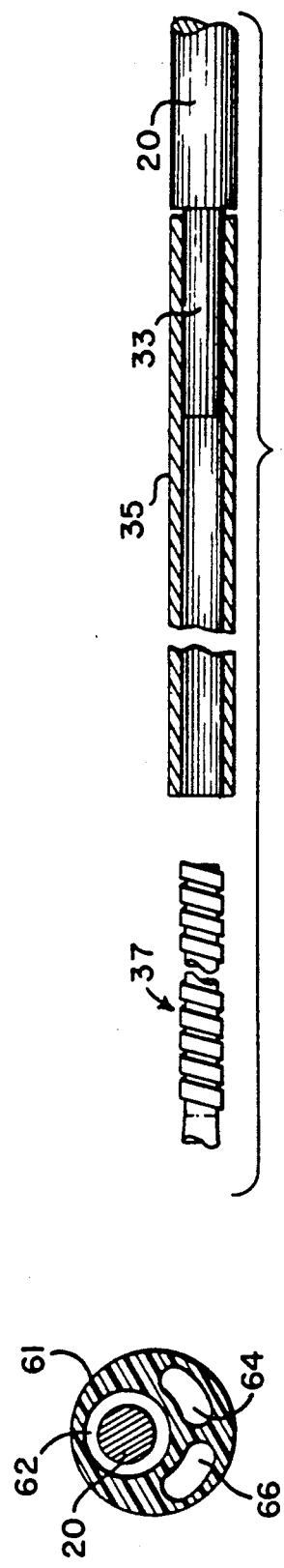
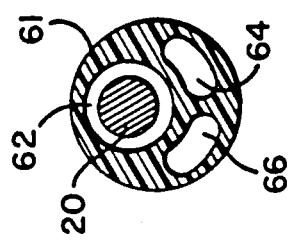
Fig. 2
Fig. 3
Fig. 4

BALLOON CATHETER AND LOCKING GUIDEWIRE SYSTEM

FIELD OF THE INVENTION

This invention relates to percutaneous transluminal angioplasty and to a low profile balloon catheter and guidewire system which allows exchange of the catheter while the guidewire remains at a selected location.

BACKGROUND OF THE INVENTION

In recent years, percutaneous transluminal angioplasty has become a common procedure for use in treating obstructions (stenoses) in an artery. The most common type of this treatment involves the use of a balloon dilatation catheter that is advanced through the patient's arteries into the stenosis and then is expanded under pressure to dilate the stenosis. The dilation results in improved blood flow and circulation in the treated artery.

When angioplasty is performed on the coronary arteries, the procedure is referred to generally as percutaneous transluminal coronary angioplasty (PTCA). PTCA is a less complex alternative to coronary bypass surgery. The PTCA procedure is of relatively short duration and involves puncturing the skin and an artery (usually the femoral artery in the patient's leg) to provide access to the patient's arterial system for the PTCA balloon dilatation catheter. The PTCA catheter is manipulated and guided through the patient's arteries with the aid of a guidewire to the site of the coronary stenosis. The balloon portion of the catheter is advanced into the stenosis and then is inflated to enlarge the lumen of the artery through the stenosed region.

One method for guiding the PTCA catheter to the site of a stenosis, referred to as the over-the-wire method, is described in U.S. Pat. No. 4,545,390 to Leary, the disclosure of which is hereby incorporated by reference. The method involves the use of a slender flexible guidewire which is advanced through the patient's vascular system until its distal end is at the desired location. The direction of guidewire travel is controlled by the physician who can monitor the position of the guidewire fluoroscopically. Once the guidewire has been navigated to the desired location, the balloon dilatation catheter is advanced over the guidewire, the wire being received in a guidewire lumen that extends through the catheter. The guidewire thus simply and automatically guides the dilatation catheter directly to the intended region.

Some obstructions, due either to their location or geometry, are very difficult to access or dilate. More specifically, in some cases, the stenosis is located within or beyond a highly tortuous artery making it very difficult to reach. In other cases, the stenosis occludes most of the artery and presents only a very narrow opening, making it very difficult to cross for proper placement of the balloon portion of the dilatation catheter. In even more complicated cases, these two conditions are combined.

Generally, a stenosis with a more narrow opening requires use of a balloon catheter having a corresponding smaller deflated cross-section, a characteristic referred to as having a low profile. In the over-the-wire systems described previously, the collapsed balloon profile has been reduced by reducing both the outside diameter of the catheter shaft in the region of the balloon and the inside diameter of its guidewire lumen. This reduced diameter permits the balloon, when evacuated and folded around the catheter body, to have a very small profile. There is a minimum limit, however, to which the guidewire lumen may be reduced, since in an over-the-wire system the physician must be able to pass the catheter over the guidewire and also withdraw the guidewire through the guidewire lumen. Thus, the guidewire lumen must always be wide enough to allow the guidewire to pass completely therethrough. A typical over-the-wire catheter has a shaft outer diameter of the order of 0.050 inches.

Alternatively, dilatation catheters having integral (non-removable) guidewires have been developed. Such catheters also are referred to as "fixed wire" catheters. Examples of such fixed guidewire catheters are described in U.S. Pat. Nos. 4,616,653; 4,573,470; 4,641,654 and 4,554,929. In these systems, the guidewire is an integral part of the catheter and is not separable from the catheter shaft. This allows a catheter of lower profile to be used because it eliminates the need to provide a guidewire lumen wide enough to allow the guidewire to pass therethrough.

The inability to separate the guidewire from the catheter in a fixed wire catheter presents some difficulties, however, because it does not allow the catheter to be exchanged for another catheter over the guidewire. The ability to perform a catheter exchange is desirable in that it allows the physician to change balloon sizes as may be desired for a number of reasons and purposes. Typically, in an over-the-wire catheter, catheter exchanges are accomplished by attaching an extension wire to the proximal end of the guidewire, removing the indwelling catheter from the patient over the extended guidewire and then sliding the new catheter along the extended guidewire to the site of the stenosis. The guidewire extension then may be detached from the guidewire. Such a procedure is described in U.S. patent application Ser. No. 07/206,008, filed June 13, 1988. In contrast, when using a fixed guidewire catheter, the catheter and guidewire necessarily are removed together, as a unit. Placement of a subsequent catheter requires that a new guidewire or catheter with an integral guidewire be inserted into the patient's arteries and re-navigated back to the stenosis thereby increasing the time required for the procedure and risk to the patient.

There is a need, therefore, for a catheter that has the low profile advantages of a fixed guidewire catheter, but which enables catheter exchanges to be performed without losing guidewire position. It is an object of the present invention to provide such a catheter arrangement.

SUMMARY OF THE INVENTION

The present invention provides a catheter system employing the combination of a low profile, multi-lumen dilatation catheter having the low profile and handling characteristics of fixed guidewire catheters, yet which enables catheter exchanges to be performed over an extendably guidewire. The system includes a steerable guidewire having an elongate flexible shaft and a highly flexible distal segment, preferably in the form of a helical coil, attached to the end of the shaft. The guidewire region that is intended to be disposed within the balloon portion of the catheter is of reduced diameter. The catheter includes a flexible elongate shaft and a dilatation balloon mounted to the end of the shaft. An inflation lumen and a guidewire lumen extend through the catheter shaft, the inflation lumen communicating with the interior of the balloon for inflation and deflation of the balloon and the guidewire lumen extending fully to and terminating in an outlet opening at the distal tip of the shaft.

In order to provide an arrangement with a low profile in the balloon region, the shaft of the catheter that extends through the balloon region is of reduced diameter, as permitted by the reduced diameter of the guidewire in that portion and, consequently, because the guidewire lumen in that portion of the catheter shaft also may be of a reduced diameter. The passageway defined by the guidewire lumen is, at no point, smaller in diameter than the largest diameter of the guidewire shaft. The diameter of the distal portion of the catheter shaft is comparable to the diameter of the distal helical coil of the guidewire such that the guidewire may not be removable through the catheter lumen. The catheter, however, may ge withdrawn with respect to the guidewire while the guidewire is maintained stationary. To that end, the proximal end of the guidewire is provided with a connector means by which an extension wire may be attached to the proximal end of the guidewire. The extension wire provides a means by which some portion of the guidewire, or the extension, will ge exposed so as to be grippable by the physician or an assistant while the catheter is withdrawn proximally over the guidewire and its extension. The catheter then can be replaced with another catheter as desired by the physician.

In order to facilitate operation of the guidewire and catheter as a unit, in the manner of a fixed wire catheter, a locking arrangement is provided at the proximal end of the catheter. The locking arrangement enables the proximal end of the guidewire to be securely locked to the proximal end of the catheter so that they may be manipulated and navigated in unison.

In one mode of operation, the catheter and guidewire are locked together at their proximal ends so that both can be manipulated and steered together. Then operated in this manner, the system operates as a fixed wire dilatation catheter. In a second mode of operation, the catheter and guidewire are not locked together, and the guidewire can be manipulated independently of the catheter. In this second mode of operation, the guidewire can be extended at its proximal end and the catheter exchanged for another catheter while maintaining the position of the distal end of the guidewire in the stenosis.

The system provides a catheter having a profile and handling characteristics similar to those of fixed guidewire catheters while providing a means by which the catheter can be withdrawn and exchanged without losing the position of the guidewire in the artery. Thus, it is not necessary to renavigate a new guidewire to the stenosis.

It is among the general objects of the invention to provide a balloon dilatation catheter system that has the low profile advantages of a fixed wire system yet which also permits a catheter exchange to be performed without losing guidewire position.

Another object of the invention is to provide a catheter system including a balloon dilatation catheter and a steerable guidewire in which the guidewire may be manipulated independently of the catheter or may be manipulated, as a unit, together with the catheter.

A further object of the invention is to provide a catheter and guidewire system of the type described in which the proximal end of the catheter is provided with means for detachably locking the guidewire to the proximal end of the catheter.

BRIEF DESCRIPTION OF THE DRAWINGS

The foregoing and other objects and advantages of the invention will be appreciated more fully from the following further description thereof with reference to the accompanying drawings wherein:

FIG. 2 is an enlarged fragmented, cross-sectional illustration of the distal portion of the balloon dilatation catheter and guidewire system shown in FIG. 1;

FIG. 3 is a partial cross-sectional view of the proximal end of a guidewire showing a portion of the connector arrangement for attaching an extension wire thereto; and FIG. 4 is a transverse cross-sectional illustration of the shaft of one embodiment of a dilatation catheter and guidewire system of the present invention.

DETAILED DESCRIPTION OF THE INVENTION

Figure 1:
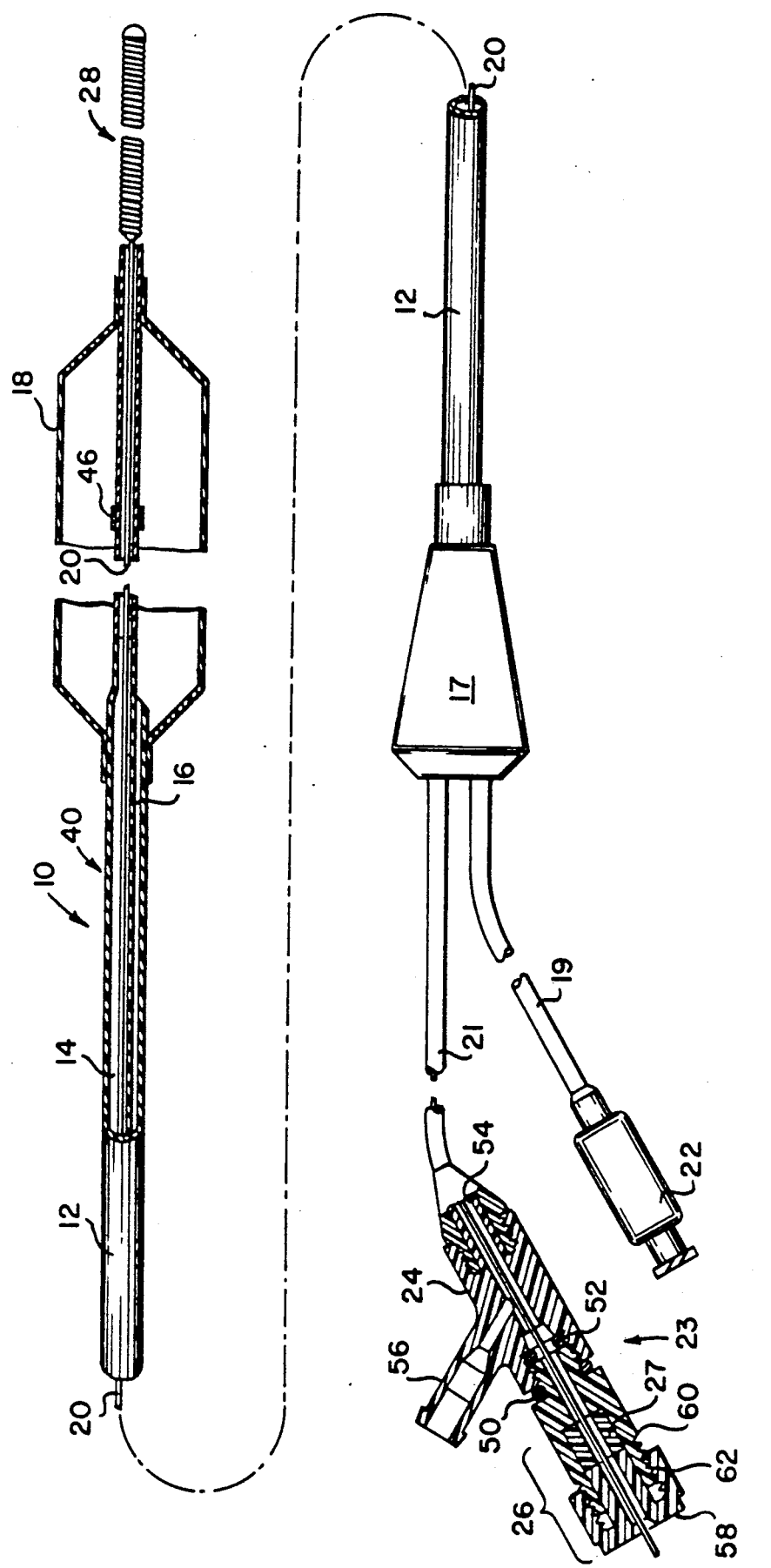
FIG. 1 is a side elevational, fragmented, partly sectional illustration of a balloon dilatation catheter and guidewire system of the present invention.

Referring to FIG. 1, the dilatation catheter/guidewire system 10 of the present invention includes an elongate flexible catheter shaft 12 formed from any of a number of suitable polymeric materials commonly used for such catheters. The shaft has a guidewire lumen 14 adapted to receive a guidewire 20 and at least one inflation lumen 16. The catheter may be of the order of 135 cm long. The diameter of the shaft 12 may be comparable to that of fixed guidewire catheters, about 0.030 inches. An inflatable balloon 18 is mounted on the distal end of the catheter and is in communication with the inflation lumen. The balloon may be formed as described in U.S. Pat. No. 4,490,421 to Levy.

A molded Y-fitting 17 is integrally attached to the proximal end of the shaft 12 and serves to form an internal connection between the lumens 14, 16 and a pair of flexible proximal tubes 19, 21. Tubes 19 and 21 communicate with, respectively, the inflation lumen 16 and the guidewire lumen 14. Tube 19 can terminate in a standard luer fitting 22. The proximal end of tube 21 has a rotating, sealable adapter assembly 23 attached thereto. The adapter assembly 23 may include a Y-fitting 24 which is secured to the proximal end of tube 21 and a rotatable, lockable element 26, such as a Tuohy-Borst adapter, which is attached to the Y-fitting 24 at rotating joint 50. An O-ring 52 serves to create a dynamic, rotational seal between the rotatable element 26 and the Y-fitting 24 thus enabling the lockable element 26 to be rotated without leaking. The adapter assembly 23, has a lumen 54 which communicates through tube 21 with the guidewire lumen 14 of the catheter shaft 12 and through which the guidewire can pass. A sidearm 56 is provided on the Y-fitting 24 to allow fluid communication with the adapter lumen 54, and consequently, with the guidewire lumen 16. The rotatable lockable element 26 comprises an end cap 58 which is threaded into a body portion 60 by threads 62 and which contains a compressible bushing 27. The bushing may be formed of a variety of resilient, compressible materials, however, a silicone elastomer is preferred.

In use, the guidewire 20 passes through the lumen 54 of adapter 23. When the end cap 58 is loosened, the compressible bushing 27 is relaxed and in its expanded configuration. In this configuration, the unit is unlocked and the guidewire can be rotated and moved axially with respect to the catheter. When the end cap 58 is tightened, however, it compresses the bushing 27. The force on the compressible bushing 27 causes the brushing to constrict about the guidewire extending through the brushing 27. The guidewire thus is sealed and locked to the catheter. When so engaged, axial movement of the guidewire is prevented. When locked to the catheter in this manner, the guidewire can still be rotated by rotatable element 26. The ability to rotate the guidewire allows it to be steered, even while locked to the catheter, to a selected site within the vasculature of a patient. When so locked together, the catheter 12 and the guidewire 20 are manipulated in unison in a manner similar to that of a catheter having an integral, fixed guidewire. When unlocked, the guidewire 20 can be rotated and advanced independently of the catheter.

As shown more clearly in FIG. 2, the extendable, steerable guidewire 20 comprises a shaft 30 which may be formed from stainless steel, having a tapered distal portion 29 and a tip portion 28 attached at its distal end. The tip portion 28 can comprise a helical coil 32 secured to the distal end of the core wire by suitable means such as a solder joint 34. A tip weld 36 is affixed at the extreme distal end of the coil to provide a rounded end to the guidewire to prevent injury to the patient as the guidewire is advanced and manipulated. The coil 32 and tip weld 36 can be fabricated of any of a variety of materials well-known in the art, such as described in the aforementioned patents, radiopaque materials such as platinum and gold being preferred.

In a preferred embodiment, the guidewire tip portion 28 has a diameter of between about 0.016 inches and about 0.017 inches and may be of the order of one to two inches long. The shaft 30 may be of the order of 0.012 inches in diameter in its proximal, untapered portion that extends over most of the length of the catheter. The tapered portion 29 of the wire 30 may extend over a length of about 4-7 cm and may taper to a diameter of about 0.004" to 0.006". A slender shaping or safety ribbon 31, approximately 0.001 inches by 0.003 inches in cross-section may extend from the end of the wire 30 to the tip weld 36.

The extreme proximal end of the guidewire shaft 30 is shown in FIG. 3. The proximal end of the shaft 30 may be provided with a cylindrical portion 33 which mates with and is securely attached to a tubular socket 35 adapted to receive a guidewire extension wire, the distal end of which is shown diagrammatically at 37. The details of the fitting 33, the socket 35 and the preferred guidewire extension system are described in U.S. patent application Ser. No. 07/206,008 filed June 13, 1988, which is incorporated herein by reference, in its entirety. As stated previously, the guidewire extension system allows the catheter to be exchanged while maintaining the position of the distal end of the guidewire in the stenosis.

The catheter 12 can be of coaxial or of extruded multi-lumen construction, or a combination thereof, and preferably is formed from a flexible polymeric material such as a polyethylene. In the embodiment shown in FIGS. 1 and 2, the catheter comprises a multi-lumen shaft 12 having a catheter tip segment 48 affixed thereto at tip joint 44. The catheter tip 48 preferably is formed from a polyimide and can be joined to the catheter shaft by any of a variety of methods known in the art, such as by heat fusion or adhesive. Alternatively, the catheter shaft 12 and the catheter tip 48 can be of single-piece construction in which the tip 48 is heat molded and formed at the distal end of the catheter shaft 12 during shaft fabrication. The catheter tip 48 defines an extension of the guidewire lumen 14 and terminates in a distal outlet orifice 25. When the catheter shaft 12 and catheter tip 48 are formed as separate pieces, the distal end of the catheter shaft, in the region of the guidewire lumen 14, preferably is necked down during assembly to merge smoothly with the proximal end of the tip 48. The necking down can be accomplished using heat and pressure molding. The catheter tip 48 may be of the order of twelve inches long and is of substantially smaller diameter than the more proximal portion of the shaft 12, having an outer diameter of the order of 0.014-0.016 inches. The reduced diameter of the distal portion of the catheter shaft facilitates collapse of the balloon 18 to a very low profile. Correspondingly, the inner diameter of the guidewire lumen 14, which exits the tip at the distal outlet orifice 25 is very small, of the order of 0.012-0.014 inches.

The inflation lumen 16 terminates proximally of the catheter tip 48 and communicates with the interior of the dilatation balloon 18. The balloon 18 can ge constructed of a variety of polymeric materials, however polyethylene terephthalate (PET) is preferred. The balloon 18 may be adhesively attached at its ends to the catheter shaft by an appropriate adhesive such as cyanoacrylate. At least one radiopaque marker band 46 may be located on the tip portion 38 of the catheter below the balloon to allow fluoroscopic visualization of balloon position during use. Also a radiopaque marker (not shown) may be located on the catheter shaft proximally of the balloon.

The interior diameter of the guidewire lumen 14 at the distal end of the catheter is large enough to receive and pass over the guidewire shaft 30 until it reaches the guidewire tip portion 28. In the preferred embodiment, the interior diameter of the guidewire lumen 14 at its distal end is about 0.012 inches to about 0.014 inches. It will be appreciated that the catheter tip 48 in the illustrated embodiment has an interior diameter less than the outer diameter of the guidewire tip 28. Consequently, it is possible to employ a catheter tip 48 having a smaller outer diameter, approximately equal to that of the guidewire tip 28. Although such a design does not allow the guidewire 20 to be withdrawn from the catheter, since the guidewire tip is unable to pass through the distal outlet orifice 25, it has the advantage of providing a relatively smooth transition between the guidewire tip 28 and the catheter tip 48 at the distal end of the device. Such a configuration is desirable because it does not result in discontinuities along the length of the catheter shaft which can inhibit catheter movement.

The use of the adapter assembly 23 allows the guidewire 20 to be sealingly locked to the catheter in a manner which prevents axial movement of the guidewire relative to the catheter while still allowing rotation of the guidewire. Thus, in the locked configuration, the catheter and guidewire may be axially advanced or withdrawn as a single unit, in the manner of a conventional low profile fixed integral wire catheter. Since the guidewire can be rotated while locked to the catheter, it is possible to steer the locked unit to a desired location within the vasculature of a patient. Alternatively, the adapter 23 can be loosened thereby enabling the physician to advance the guidewire independently of the catheter. Thus, when the guidewire is locked to the catheter, the system can be operated in a manner similar to that of a catheter having an integral guidewire, and when the guidewire is unlocked from the catheter, the system can be operated in a manner similar to that of an over-the-wire catheter/guidewire system.

The system is not intended to be limited to a catheter having dual lumen construction. Rather, coaxial catheters and catheters having three or more lumens can be used. For example, FIG. 4 is a cross-sectional axial view of a three lumen catheter in a region proximal to the termination of the inflation lumens. The shaft 61 contains a guidewire lumen 62 and two inflation lumens 64 and 66. A guidewire 20 is positioned within the guidewire lumen. The inflation lumens 64 and 66 are asymmetrical and have a minimum interior dimension of about 0.010 inches. The guidewire lumen, is circular and in the region proximal to the balloon, has an interior diameter of about 0.016 inches. The guidewire has a cross-sectional diameter of about 0.010 inches.

The dilatation catheter/guidewire system described herein combines the advantages of over-the-wire and fixed, integral guidewire systems. As in a fixed guidewire system, the present system can have a very low profile, with a catheter shaft of the order of 0.030 inches and can be easily manipulated by a physician. Unlike a fixed guidewire system, however, the present system does not have the disadvantage of the inability to perform a catheter exchange without losing guidewire position. The catheter can be withdrawn from the patient without disturbing the guidewire position. The present system also allows the guidewire to accommodate an extension 37 at its proximal end to allow the catheter to be exchanged, as described in more detail in aforesaid application U. S. Ser. No. 07/206,008. The present system also allows independent wire movement and excellent steerability while providing the option of sealingly locking the guidewire and catheter together to allow operation as a single unit.

The guidewire/catheter system described herein may be advanced to the coronary arteries through a previously placed guide catheter, as is well known and common practice.

Once the guidewire and dilatation catheter have been advanced through the guide catheter and into the coronary arteries to a point where the balloon is positioned within the obstruction, the position can be verified fluoroscopically by the radiopaque markers. Injecting a radiopaque contrast fluid through the guide catheter allows visualization of the anatomy. Additionally, in one mode of operation, referred to as a "half exchange", maximum flow of the contrast fluid is achieved while maintaining a selected guidewire position. In this mode of operation, the guidewire is extended with an extension wire 37 and the catheter is partially withdrawn from the patient over the guidewire extension 37. A radiopaque contrast fluid then is injected through the guiding catheter while the guidewire remains in place. This procedure allows a maximum dilatation assessment while maintaining the previously acquired guidewire position in the vasculature.

Additionally, the low profile of the balloon catheter allows an adequate amount of the contrast fluid to be injected around the balloon catheter while the balloon catheter is resident in the guiding catheter. Since the balloon portion is not withdrawn through apparatus at the proximal end of the guiding catheter, the likelihood of balloon damage is minimized.

It should be noted that the dimensions described herein are applicable particularly to dilatation catheters of the 3 French (0.039 inches) size. These dimensions have been selected for purposes of illustration and are not intended to be limiting. Although the invention can be applied to catheters having a wide range of sizes, it is particularly well suited to applications in which a low profile design is required.

Additionally, specified materials of construction are not intended to be limiting. Rather, unless otherwise noted, the catheter, balloon, guidewire and related apparatus can be constructed of any material commonly used in the art.

Thus, from the foregoing it will be appreciated that the invention provides advantages of over-the-wire and fixed integral wire catheter systems without their respective limitations. The invention provides a catheter system that in one mode acts as a low profile catheter adapted to be steered and passed through narrow stenoses while enabling catheter exchanges to be performed without losing guidewire position. Moreover these advantages are achieved in a system that also enables independent guidewire manipulation and permits dye injection to be made through the catheter.

It should be understood, however, that the foregoing description of the invention is intended to be merely illustrative thereof and that other modifications and embodiments may be apparent to those skilled in the art without departing from the spirit.

Having thus described the invention, what I desire to claim and secure by Letters Patent is:

1. A dilatation catheter and guidewire comprising:
   an elongate flexible catheter shaft having a proximal end, a distal end, a guidewire lumen and an inflation lumen;
   a dilatation balloon mounted on the distal end of the shaft with the inflation lumen being in communication with the interior of the balloon;
   a guidewire extending through the guidewire lumen, the guidewire comprising a shaft adapted to extend fully through the guidewire lumen and a flexible distal segment affixed to the distal end of the guidewire shaft, the flexible distal segment extending distally beyond the distal end of the catheter shaft;
   means for attaching an extension wire to the proximal end of the guidewire; and
   means for releasably locking a proximal portion of the guidewire to the proximal portion of the catheter;
   the guidewire lumen being larger in diameter than the outer diameter of any portion of the guidewire shaft proximal to the flexible distal segment; and
   the locking means, when locked, allowing the guidewire to be rotated relative to the catheter while preventing relative axial movement between the guidewire and the catheter, and when unlocked, allowing the guidewire to be rotated and advanced independently of the catheter.

2. A dilatation catheter and guidewire as in claim 1 wherein the guidewire shaft, in the region of the balloon, is of a reduced diameter.

3. A dilatation catheter and guidewire as in claim 1 wherein the interior diameter of the guidewire lumen at the distal end is less than the interior diameter of the guidewire lumen at the proximal end.

4. A dilatation catheter and guidewire as in claim 1 wherein the outer diameter of the distal end of the catheter shaft corresponds substantially to the outer diameter of the distal segment of the guidewire.

5. A dilatation catheter and guidewire as in claim 4 wherein the dilatation catheter comprises a low profile balloon dilation catheter.

6. A dilatation catheter and guidewire as in claim 5 wherein the balloon comprises polyethylene terephthalate.

7. A dilatation catheter and guidewire as in claim 1 wherein the guidewire comprises a stainless steel shaft having a flexible distal segment at its distal end.

8. A dilatation catheter and guidewire as in claim 7 wherein the flexible distal segment of the guidewire comprises a helical coil.

9. A dilatation catheter and guidewire as in claim 1 wherein the outer diameter of the flexible distal segment of the guidewire is greater than the diameter of the guidewire lumen at the extreme distal end of the catheter.

10. A dilatation catheter and guidewire as in claim 1 wherein the catheter shaft comprises a main catheter body having a catheter tip segment affixed to the distal end thereof.

11. A dilatation catheter and guidewire as in claim 1 wherein the catheter shaft comprises polyethylene.

12. A dilatation catheter and guidewire as in claim 1 wherein the locking means has a guidewire lumen therethrough and comprises a catheter fitting portion, a body portion containing a compressible bushing and an end cap, the body portion and catheter fitting portion being connected by a . rotating, dynamic seal.

13. A dilatation catheter and guidewire as in claim 12 wherein the compressible bushing comprises a silicone elastomer.

14. A low profile dilatation catheter and guidewire comprising:
- an elongate flexible catheter shaft having a proximal end, a distal end, a guidewire lumen and an inflation lumen;
- a dilatation balloon mounted on the distal end of the shaft with the inflation lumen being in communication with the interior of the balloon;
- a guidewire extending through the guidewire lumen, the guidewire comprising a shaft having a maximum cross-sectional diameter of approximately 0.012 inches adapted to extend fully through the guidewire lumen and a flexible distal segment having a cross-sectional diameter of approximately 0.016 inches to approximately 0.017 inches affixed to the distal end of the guidewire shaft and extending distally beyond the distal end of the catheter shaft;
- means for attaching an extension wire to the proximal end of the guidewire, and
- means for releasably locking a proximal portion of the guidewire to the proximal portion of the catheter;
- the guidewire lumen having a minimum cross-sectional diameter of approximately 0.014 inches to approximately 0.016 inches; and
- the locking means, when locked, allowing the guidewire to be rotated relative to the catheter while preventing relative axial movement between the guidewire and the catheter, and when unlocked, allowing the guidewire to be rotated and advanced independently of the catheter.

15. A low profile dilatation catheter and guidewire as in claim 14 wherein the balloon comprises polyethylene terephthalate.

16. A low profile dilatation catheter and guidewire as in claim 14 wherein the catheter shaft comprises polyethylene.

17. A low profile dilatation catheter and guidewire as in claim 14 wherein the interior diameter of the guidewire lumen at the distal end is less than the interior diameter of the guidewire lumen at the proximal end.

18. A dilatation catheter and guidewire as in claim 14 wherein the locking means has a guidewire lumen therethrough and comprises a catheter fitting portion, a body portion containing a compressible bushing and an end cap, the body portion and catheter fitting portion being connected by a rotating, dynamic seal.

19. A low profile dilatation catheter and guidewire as in claim 18 wherein the compressible bushing comprises a silicone elastomer.

20. A low profile dilatation catheter and guidewire as in claim 14 wherein the catheter shaft comprises a main catheter body having a catheter tip segment affixed to the distal end thereof.

21. A dilatation catheter and guidewire as defined in either of claims 1 or 14 dimensioned and constructed to be percutaneously insertable into a patient's arteries and advanceable into the coronary arteries.

22. A dilatation catheter as defined in either of claims 1 or 14 wherein said catheter comprises a coronary angioplasty dilatation catheter.

23. A dilatation catheter and guidewire comprising:
- an elongate flexible catheter shaft having a proximal end, a distal end, a guidewire lumen and an inflation lumen;
- a dilatation balloon mounted on the distal end of the shaft with the inflation lumen being in communication with the interior of the balloon;
- a guidewire extending through the guidewire lumen, the guidewire comprising a shaft adapted to extend fully through the guidewire lumen and a flexible distal segment affixed to the distal end of the guidewire shaft, the flexible distal segment extending distally beyond the distal end of the catheter shaft;
- a connector element at the proximal end of the guidewire adapted to be connected to an extension wire; and
- a guidewire locking member at the proximal end of the catheter adapted to releasably lock a proximal portion of a guidewire to the catheter;
- the guidewire lumen being larger in diameter than the outer diameter of any portion of the guidewire shaft proximal to the flexible distal segment; and
- the locking member being rotatably mounted with respect to the catheter to enable the guidewire to be rotated relative to the catheter while preventing relative axial movement between the guidewire and the catheter, the locking member being further constructed so that when unlocked, the guidewire can be rotated and advanced independently of the catheter.

24. A catheter as defined in claim 23 dimensioned to be percutaneously insertable into a patient's arteries and advanceable to the coronary arteries.

25. A catheter as defined in claim 23 wherein said catheter comprises a coronary angioplasty catheter.

* * * * *